(12) United States Patent
Lambert et al.

(10) Patent No.: US 7,700,044 B2
(45) Date of Patent: *Apr. 20, 2010

(54) CHEMICAL VAPOR SENSOR

(75) Inventors: David K. Lambert, Sterling Heights, MI (US); Larry M. Oberdier, Royal Oak, MI (US); Christopher M. Thrush, Shelby Township, MI (US)

(73) Assignee: Delphi Technologies, Inc., Troy, MI (US)

( * ) Notice: Subject to any disclaimer, the term of this patent is extended or adjusted under 35 U.S.C. 154(b) by 1045 days.

This patent is subject to a terminal disclaimer.

(21) Appl. No.: 11/033,677

(22) Filed: Jan. 12, 2005

(65) Prior Publication Data

US 2006/0154377 A1 Jul. 13, 2006

(51) Int. Cl.
*G01N 30/96* (2006.01)
(52) U.S. Cl. .................. 422/88; 422/85.05; 422/82.09; 422/83; 436/167; 250/349; 250/343; 250/345; 250/344; 356/36
(58) Field of Classification Search ............. 422/82.05, 422/82.09, 83, 88; 436/167; 250/349, 343, 250/345, 344; 356/36
See application file for complete search history.

(56) References Cited

U.S. PATENT DOCUMENTS

| 3,792,272 | A | | 2/1974 | Harte et al. | |
|---|---|---|---|---|---|
| 5,142,143 | A | * | 8/1992 | Fite et al. | 250/288 |
| 5,422,485 | A | * | 6/1995 | Bowlds | 250/343 |

(Continued)

FOREIGN PATENT DOCUMENTS

EP 0633471 1/1995

(Continued)

OTHER PUBLICATIONS

Pogodina O A et al.: "Combination of Sorption Tube Sampling and Thermal Desorption with Hollow Waveguide FT-IR Spectroscopy for Atmospheric Trace Gas Analysis: Determination of Atmospheric Ethene at the Lower ppb Level" Analytical Chemistry, American Chemical Society. Columbus, US, vol. 76, No. 2, Dec. 9, 2003, pp. 464-468, XP002374165 ISSN: 003-2700 *figure 1* *p. 465, left-hand column, last paragraph—p. 466, left-hand column, paragraph 1*.

(Continued)

*Primary Examiner*—Lyle A Alexander
*Assistant Examiner*—Dennis M White
(74) *Attorney, Agent, or Firm*—Jimmy L. Funke

(57) ABSTRACT

A chemical vapor sensor is provided that passively measures a chemical species of interest with high sensitivity and chemical specificity. In an aspect, ethanol vapor in a vehicle cabin is measured, and sufficient sensitivity is provided to passively detect a motor vehicle driver that exceeds a legal limit of blood alcohol concentration (BAC), for use with vehicle safety systems. The sensor can be situated in an inconspicuous vehicle cabin location and operate independently without requiring active involvement by a driver. A vapor concentrator is utilized to amplify a sampled vapor concentration to a detectible level for use with an infrared (IR) detector. In an aspect, in comparison to conventional chemical sensors, the sensitivity of detection of ethanol vapor is increased by a factor of about 1,000. Further, a single channel of infrared detection is utilized avoiding spurious infrared absorption and making the chemical vapor sensor less costly to implement.

23 Claims, 6 Drawing Sheets

U.S. PATENT DOCUMENTS

| | | | |
|---|---|---|---|
| 6,067,167 A * | 5/2000 | Atkinson et al. | 356/437 |
| 6,313,464 B1 | 11/2001 | Schrader | |
| 6,319,724 B1 * | 11/2001 | Lewis et al. | 436/149 |
| 2004/0141171 A1 * | 7/2004 | Lambert et al. | 356/36 |

FOREIGN PATENT DOCUMENTS

| | | |
|---|---|---|
| EP | 1441212 | 7/2004 |
| JP | 2000/241313 | 9/2000 |
| WO | 2006/055458 | 2/2006 |

OTHER PUBLICATIONS

U.S. Appl. No. 10/348,496, filed Jan. 21, 2003.

* cited by examiner

CHEMICAL VAPOR SENSOR

FIELD OF THE INVENTION

The invention relates generally to a chemical sensor, and more particularly to passively measuring, with high sensitivity and chemical specificity, a chemical species of interest, for use in safety systems.

BACKGROUND OF THE INVENTION

Intoxicated drivers are a major cause of traffic accident fatalities in the United States. A recent NHTSA report showed that 40% of the total accident fatalities in the U.S. in the year 2003 were alcohol related. More specifically, 12,373 motor vehicle occupants were killed in crashes that involved a blood alcohol concentration (BAC) of 0.08% or higher. This equates to over 33% of the 37,132 U.S. motor vehicle fatalities in 2003. In addition to the societal impact, the cost of such crashes in the U.S. is about $40 billion per year. It is well established that the rate of fatal traffic accidents per mile traveled is related to a driver's (BAC) and that there is a correlation between impairment in driving skills and the driver's BAC. The definition of drunk driving in the U.S. involves a BAC level of either 0.08% or 0.10%, depending on the particular state law. Moreover, the states of the U.S. that currently have a 0.10% BAC limit have passed laws lowering the BAC limit to 0.08%, to take effect soon. Various approaches to combat drunk driving have been utilized. The following existing approaches require active involvement of a vehicle driver.

Ethanol concentration in human breath is a good indication of BAC. Inside the human lung, there is a chemical equilibrium between the concentration of ethanol in the air and the concentration of ethanol in an individual's blood. An approach to combat drunk driving, which utilizes this notion of ethanol concentration in human breath, uses an electrochemical sensor to measure ethanol concentration in air. For law enforcement purposes, an electrochemical sensor is built into an object such as a clipboard or flashlight that a police officer can, under certain circumstances, justifiably insert into a vehicle. However, currently available electrochemical sensors have a limited lifetime and typically must be replaced after about three years. To be used as an on-board component of the safety system, an ethanol sensor must have a lifetime of at least ten to fifteen years.

An additional approach to combat drunk driving uses a heated film of metal oxide that changes electrical resistance in response to ethanol concentration. Such sensors are used in commercially available "breath interlocks," sometimes mandated following a drunk driving conviction, which requires the driver to breathe into a tube to check for excess breath alcohol before the vehicle will start. However, such sensors do not have sufficient sensitivity for passive detection of a drunk driver in regard to measuring ethanol vapor in the air of a vehicle cabin. The breath sample blown into a tube is undiluted so the detection level needed is only about 210 ppm ethanol. Also, the minimum ethanol concentration that can be reliably detected with a metal oxide film is typically in the range of 10 to 50 ppm. A further disadvantage is that the response to ethanol concentration is non-linear as a function of ethanol concentration.

A further approach to combat drunk driving uses an electrochemical sensor that is pressed against an individual's skin to determine alcohol intoxication through remote detection of ethanol that evaporates from the driver's skin. This approach is an active system since contact with the driver's skin is required. The lifetime of this sensor has not been demonstrated.

U.S. patents have been issued for approaches that combat drunk driving that involve passing infrared through one of the driver's extremities, such as a finger, or using Raman spectroscopy to measure the concentration of ethanol in the fluid at the surface of the driver's eyes (i.e., U.S. Pat No. 6,574, 501). These approaches are impractical for on-board vehicle use as well.

Further approaches to combat drunk driving exist. The following approaches are passive since active involvement of the driver is not required. For example, monitoring a vehicle driver's eyes to determine driver intoxication has been attempted. The direction of the driver's gaze is monitored as they visually follow a moving object. It is believed that an intoxicated person moves their gaze direction in jumps rather than following an object's motion smoothly and continuously.

A recently published patent application (U.S. Patent Application No. 20040141171, assigned to Delphi Technologies, Inc., filed Jan. 21, 2003) provides increased sensitivity with a short path length by using a vapor concentrator. Ethanol vapor is collected by passing air that contains ethanol vapor over an adsorber for a period of time. The adsorber is then heated to release the ethanol vapor. Sensors are utilized that detect ethanol vapor by measuring its effect on the electrical conductance of a heated metal oxide film on a ceramic substrate.

Infrared detection has been used to quantify ethanol concentration in breath for law enforcement purposes, but the instruments used typically have a path length of about 1 meter making it large and bulky. For passive sensing in a vehicle cabin, utilizing this instrument, infrared detection would require a path length on the order of 100 meters. This is impractical for an on-board sensor.

SUMMARY OF THE INVENTION

A chemical vapor sensor is provided that passively measures a chemical species of interest with high sensitivity and chemical specificity in a selected area, for use in safety systems.

In an embodiment, the present invention provides for optical detection of ethanol for use in motor vehicle safety systems. Ethanol vapor in a vehicle cabin is measured, and sufficient sensitivity is provided to passively detect a motor vehicle driver (not requiring active involvement by the driver) that exceeds the legal limit of blood alcohol concentration (BAC). At the threshold of intoxication, the concentration of ethanol in breath is 210 ppm. The present invention provides for passive detection of ethanol concentration by measuring ethanol concentration in the range of 0.1 ppm to 10 ppm by volume in the cabin of a vehicle. Additionally, since drivers can exhibit a BAC of much greater than 0.08, and the vehicle cabin air may be less diluted, the present invention further provides for measuring ethanol concentrations greater than 10 ppm. In an embodiment, in comparison to known systems, the present invention increases the sensitivity of detection of ethanol vapor by a factor of about 1,000.

Further, the sensor can be situated in an inconspicuous location and operate independently without requiring active involvement by a driver. If a predetermined concentration of a chemical species is exceeded, as measured by the sensor, an appropriate safety system response can optionally be carried out. The safety system can impose requirements including requiring minimum headway distance behind a preceding vehicle, as well as constrain vehicle performance.

Features of the invention are achieved in part by increasing the sensitivity of detection of a chemical vapor. A vapor concentrator is utilized to amplify chemical vapor concentration to a detectible level for use with an infrared (IR) detector. In the case of detecting ethanol, air is passed through an adsorber for a predetermined time to collect ethanol vapor. The air flow is stopped and the adsorber is heated to release a higher concentration of ethanol vapor into an IR absorption cell. The ethanol concentration is amplified by about two orders of magnitude due to heating the adsorber. Infrared transmission by an IR source to an IR detector is used to detect the ethanol. An IR filter limits IR detector response to a band that is adsorbed by ethanol vapor. Additionally, a microcontroller instructs and carries out an appropriate safety system response if a predetermined concentration of a chemical species is exceeded.

A single channel of infrared detection is utilized, and consequently the present invention is less costly to implement. Further, since a reference channel is made unnecessary, spurious infrared absorption at the infrared wavelength of the reference channel is not a concern. Additionally, when measuring a chemical species, time resolution is not limited by the thermal time constant of the IR source, resulting in a simplified system having improved performance.

Other features and advantages of this invention will be apparent to a person of skill in the art who studies the invention disclosure. Therefore, the scope of the invention will be better understood by reference to an example of an embodiment, given with respect to the following figures.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE INVENTION

Figure 1:
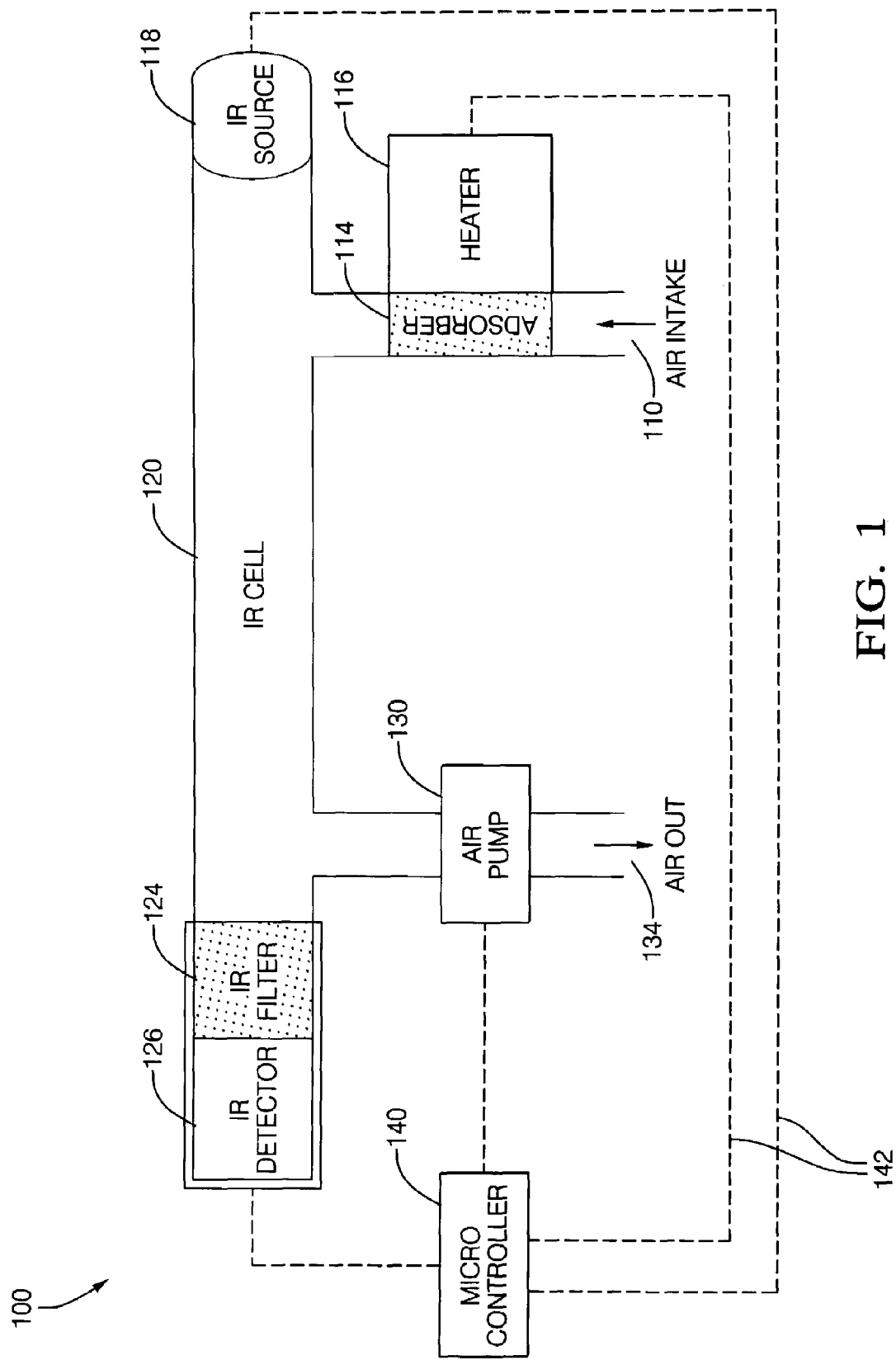
FIG. 1 is a diagrammatic sectional view of components of a chemical sensor including a vapor concentrator and microcontroller, in an embodiment of the present invention.

Exemplary embodiments are described with reference to specific configurations. Those of ordinary skill in the art will appreciate that various changes and modifications can be made while remaining within the scope of the appended claims. Additionally, well-known elements, devices, components, methods, process steps and the like may not be set forth in detail in order to avoid obscuring the invention. Further, unless indicated to the contrary, the numerical values set forth in the following specification and claims are approximations that may vary depending upon the desired characteristics sought to be obtained by the present invention.

Presently, in the United States, a driver is legally deemed intoxicated when exhibiting a blood alcohol concentration (BAC) of 0.08%, and therefore violating the law if operating a motor vehicle while intoxicated. Passively monitoring a motor vehicle driver's BAC can facilitate avoiding motor vehicle accidents caused by intoxicated drivers. The BAC measurement can be utilized to instruct a vehicle to shut down or compensate for the effect of BAC on the driver's reaction time. Passive monitoring (rather than active) senses the vehicle driver's BAC without active involvement of the vehicle driver. However, conventional ethanol vapor sensors are unsuitable for on-board passive detection of drunk drivers in regard to monitoring ethanol concentration in the air of a vehicle cabin.

A vapor sensor based on infrared transmission requires an appropriate path length. If the path length is too short, the change in detected intensity is small relative to the fluctuations in detected intensity. If the path length is too long, the detected intensity at the center of an absorption line is small. The optimum path length depends upon the chemical concentration that is to be measured. Consider, for example, a sensor that measures the fraction of light transmitted in a fixed band of optical frequency. For improved accuracy the species of interest should maintain on the order of 10% absorption in the band. In conventional chemical sensors, an absorption band near 1070 $cm^{-1}$ (9.4 µm wavelength) is typically used to detect ethanol vapor. Near the peak of the 1070 $cm^{-1}$ band, the absorption coefficient is about $2.5 \times 10^{-4}$ $(\mu mol/mol)^{-1}$ $m^{-1}$. Consequently, with an ethanol concentration of 250 ppm, a path length of 0.7 m is needed to obtain 10% absorption. At the threshold of intoxication, the concentration of ethanol in breath is about 210 ppm. For comparison, to determine the concentration of ethanol vapor in a breath sample, law enforcement typically uses an infrared-based instrument that has a 1 m path length through the breath sample.

However, for passive monitoring of ethanol, vehicle cabin air is monitored (rather than direct monitoring of a driver's breath) and an ethanol sensor consequently requires the ability to monitor a significantly reduced ethanol concentration. As further detailed below, an ethanol sensor employing passive monitoring must be capable of measuring ethanol in the range of 0.2 ppm to 10 ppm in the cabin of a vehicle. If an infrared sensor is to be used to measure an ethanol concentration on the order of 1 ppm, the optimum path length for a commercially available sensor would be on the order of 100 m. It is plainly recognized that the necessity of a 100 m path length limits its use in a vehicle. Thus, commercially available ethanol vapor sensors are too bulky for on-board use, requiring a long pathlength for infrared sensing.

The present invention provides a vapor concentrator (as further described below) that increases ethanol concentration to a level needed by an infrared (IR) detector for passive detection with vehicle cabin air, and therefore enables the detection of sub-ppm concentrations of ethanol. Further, the present invention improves chemical selectivity.

Experiment

The following experimental examples are provided for illustrative purposes and are not intended to be limiting.

The ethanol sensitivity needed to passively detect a driver at the threshold of intoxication is additionally determined by the present invention. $CO_2$ that is naturally present in human breath is used as a tracer to determine sensor measurement requirements (sensitivity required) for passive detection of ethanol in a vehicle cabin. This avoids the use of intoxicated human subjects. Ethanol and $CO_2$ do not separate significantly as exhaled breath drifts from a driver's mouth to a location where air is sampled by the passive sensor. The transport of both ethanol vapor and $CO_2$ from a driver's mouth to the sensor is dominated by convection, which is the same for both ethanol and $CO_2$. The concentration of ethanol vapor in breath is proportional to BAC, and is 210 ppm when BAC is 0.08%. The concentration of $CO_2$ in exhaled breath is approximately 36000 ppm (as compared to 370 ppm in ambient air). Like ethanol, $CO_2$ in exhaled breath comes from exchange with blood in the alveolar sacs in the lung. Based on $CO_2$ measurements with a test subject, the breath alcohol concentration at the sensor is at least 0.5 ppm for any HVAC setting (with the windows closed) at 5 minutes after a driver with BAC of 0.08 is seated in the vehicle. Some drivers breathe only half as much air as the test subject, so the ethanol sensor requires sensitivity to 0.2 ppm ethanol in air. Therefore, the sensor must be capable of measuring ethanol concentration in the range of 0.2 ppm to 10 ppm ethanol in air by volume.

Referring to the drawings wherein identical reference numerals denote the same elements throughout the various views, FIG. 1 illustrates components of the chemical sensor 100, which includes microcontroller 140 and a vapor concentrator (vapor concentrator comprising adsorber 114 and heater 116). Air is drawn into air intake 110 by means of air pump 130, passes through adsorber 114 and absorption cell 120, and released through air out 134. Air pump 130 is, for example, model TD-3LS from Brailsford and Company, Inc. It may be useful to incorporate a check valve for pressure relief in series to ensure no air flow when air pump 130 is off. Adsorber 114 adsorbs ethanol vapor and is heated by heater 116. Adsorber 114 can be comprised of carbon such as carbon molecular sieves, carbon nanotubes, and activated carbon. Alternatively, adsorber 114 can be comprised of a porous organic polymer or an inorganic material having a high surface area such as a zeolite. Adsorber 114 is, for example, a 3 mm long bed of Carboxen 1003 in a glass tube from Supelco. Heater 116 can be constructed by winding resistive wire around a glass tube that encloses adsorber 114, and fastening the resistive wire to the glass tube utilizing epoxy. IR source 118 passes infrared waves across IR absorption cell 120 to IR filter 124, for measurement by IR detector 126. IR source 118 is, for example, an electrical heater, which can be activated by controlling the current. A broad-band emitter such as an Ion Optics source, part number NL5NCC can be employed for IR source 118, when employing a 9.4 micron wavelength band. NL5NCC consists of heated filament (in air) with a calcium fluoride window that separates it from an IR cell. The calcium fluoride window is transparent at this wavelength. Similar devices that emit IR by using electrical power to raise a wire or film to an elevated temperature are available from other manufacturers. When employing a 3.4 micron wavelength band, IR source 118 can also be, for example, an incandescent lamp. IR filter 124 is used to select a range of infrared frequency or wavelength that is adsorbed by ethanol. IR detector 126 can be a thermopile employed to detect IR. The thermopile converts the incident IR into heat and uses a series array of thermocouples to measure the induced temperature rise. IR detector 126 provides an output voltage as a function of time. A microcontroller 140 instructs and coordinates (through signal lines 142) the predetermined operation of chemical sensor 100 components including air pump 130, heater 116, IR source 118 and IR detector 126.

The vapor concentrator amplifies the partial pressure of a sample gas, in an embodiment of the present invention. The amplification factor is limited by adsorber's 114 capacity to collect the species of interest. When the limit is exceeded, adsorber 114 begins to saturate, and breakthrough occurs. Let $V_B$ be the volume of sample gas that can be passed through adsorber 114 before breakthrough. Let $V_S$ be the gas volume in adsorber 114. The maximum possible amplification factor is $A=V_B/V_S$. Thus, to optimize A, the breakthrough volume should be maximized relative to the sample volume. One approach is to isolate adsorber 114 as it is heated, for example, by stopping the air flow. As an estimate, the maximum A is the ratio of the breakthrough volume to the volume of adsorber 114 itself. The concentration can alternatively be amplified by rapidly heating adsorber 114 with constant flow of air through the vapor concentrator. If this is done, the maximum concentration depends upon the number of times the air is exchanged while heating, so it is important to heat adsorber 114 rapidly.

The safety consequences of drunk driving result from impaired driving skills and extra risk taking. One approach is to give an impaired driver more time to react. The present invention provides for automatic compensation by a safety system for the slowed reaction time of a drunk driver. For example, if a predetermined concentration of ethanol is exceeded, as measured by the chemical sensor 100 (i.e., an IR sensor), an appropriate safety system response can be carried out by an engine microcontroller 140. The safety system can impose restrictive requirements and limitations including requiring or increasing a minimum headway distance behind a preceding vehicle, as well as constrain vehicle performance. Additionally, the safety system can transmit to police, through a wireless transmitter, a message that indicates a measured ethanol concentration or that the ethanol concentration in the vehicle cabin or the vehicle driver's BAC exceeds a preset level. Further, in an embodiment, in the case of a traffic accident, the safety system can alert an EMS responder, or police, that ethanol is detected. Additionally, if a predetermined level of ethanol vapor or BAC is detected, then the safety system can transmit the measured value to a flight recorder for eventual downloading by a third party.

The ethanol detection of the present invention can be employed prior to vehicle startup, and can be performed repetitively during vehicle operation. Repetitive sensing enables the present invention to monitor a driver for previously consumed alcohol that will cause the ethanol concentration in the driver's breath to increase over time, perhaps above the legal limit.

Water can condense inside IR absorption cell 120 if IR absorption cell 120 reaches a particular low temperature. This can potentially cause an error in the detection of a small concentration of a particular chemical vapor from IR transmission since the liquid water on the walls of IR absorption cell 120 can cause the intensity of transmitted IR to decrease.

In an embodiment, the present invention provides the following adjustments to chemical sensor 100: IR absorption cell 120 is heated to a temperature above the dew point of the vapor released into it from adsorber 114. Alternatively, adsorber 114 (carbon) is heated so it is on the order of 10 degrees Celsius above ambient temperature while the ethanol is being adsorbed. This limits the volume of water adsorbed by adsorber 114 to avoid exceeding the dew point when desorbed vapor is vented into IR absorption cell 120. It may be that carbon can adsorb water if it is close to the dew point. Alternatively, the inside of IR absorption cell 120 is coated with a material that prevents water droplets from nucleating, such as presently existing coatings for vehicle windshields that serve a similar function. Alternatively, the air flow is altered through IR absorption cell 120 so that exhaust from the vapor concentrator flows down the center of IR absorption cell 120, but avoids contacting the cool walls where it can condense. Alternatively, an adsorbent material is utilized that is more hydrophobic than carbon, but still adsorbs ethanol vapor.

Figure 2:
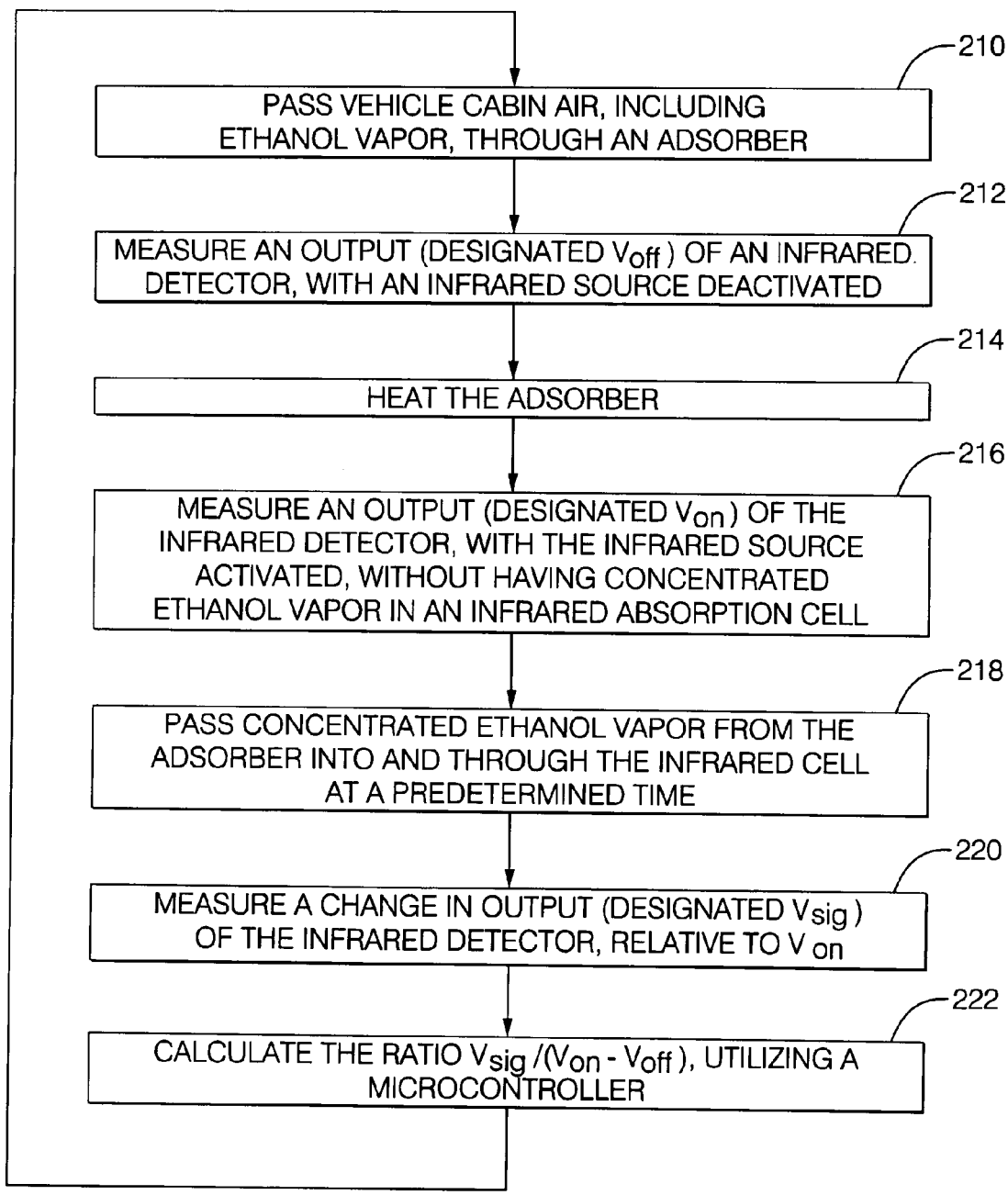
FIG. 2 is a method step illustration of the measurement of ethanol vapor with high sensitivity and chemical specificity, in accordance with an embodiment of the present invention.

FIG. 2 is a method step illustration of the measurement of ethanol vapor with high sensitivity and chemical specificity. Ethanol vapor is collected by passing ambient air into and through adsorber 114 (indicated as method step 210). The IR detector 126 provides an output voltage (designated $V_{off}$), with IR source 118 off (indicated as method step 212). The adsorber 114 is heated by heater 116 to release the captured ethanol vapor (indicated as method step 214). The IR source 118 is activated and an output voltage (designated $V_{on}$) of IR detector 126 is measured without having concentrated ethanol vapor in IR absorption cell 120 (indicated as method step 216). Concentrated ethanol vapor is passed from adsorber 114 into and through IR absorption cell 120 at a predetermined time (indicated as method step 218). Next, the change in output voltage (designated $V_{sig}$) of IR detector 126 caused by the additional infrared adsorption, relative to $V_{on}$, is measured (indicated as method step 220). As the concentration of ethanol vapor in the tube increases, there is a decrease in the IR intensity that is detected. Microcontroller 140 calculates the ratio $V_{sig}/(V_{on}-V_{off})$ (indicated as method step 222).

Figure 3:
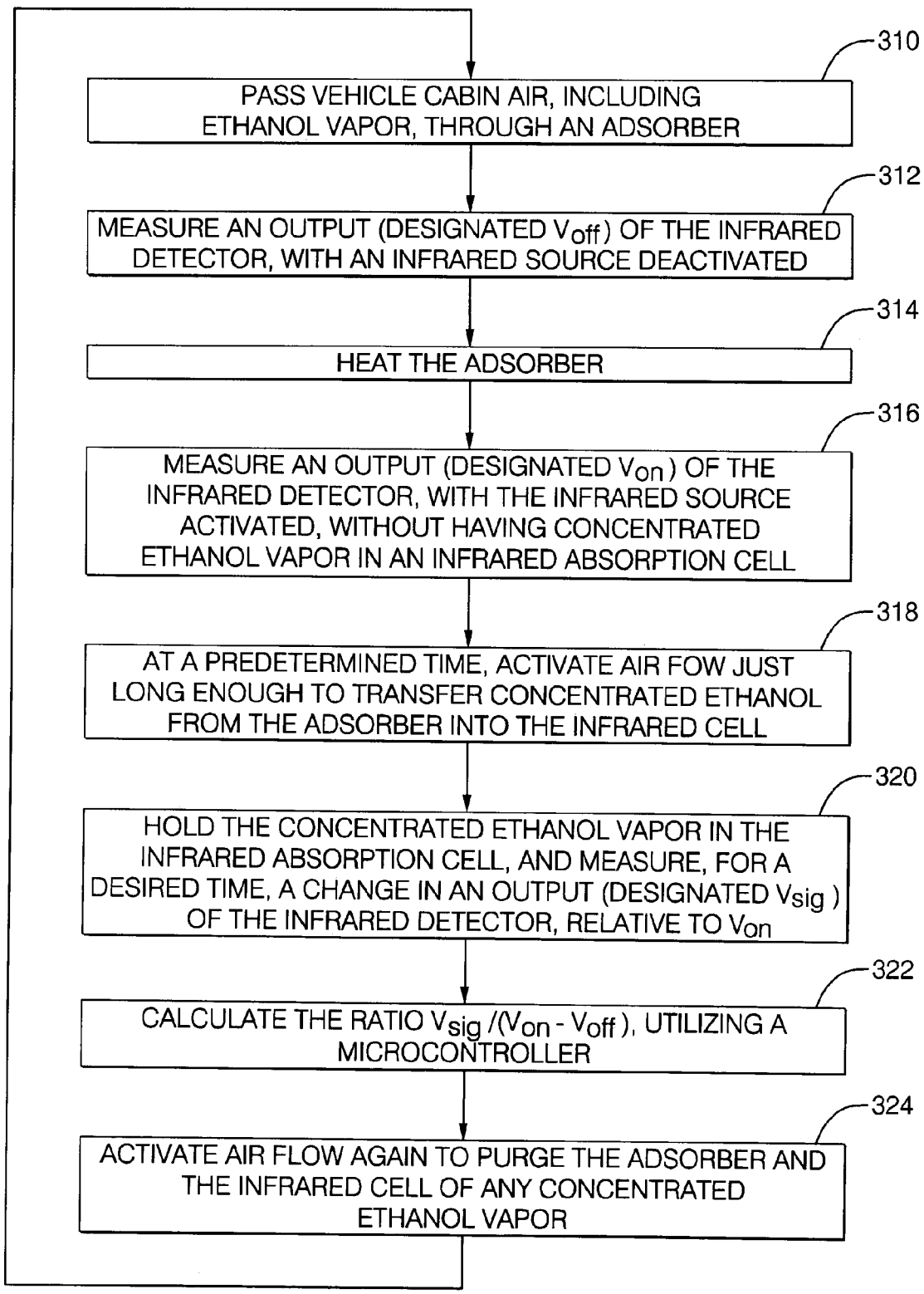
FIG. 3 is an alternative method step illustration of the measurement of ethanol vapor with high sensitivity and chemical specificity, in accordance with an embodiment of the present invention.

FIG. 3 is an alternative method step illustration of the measurement of ethanol vapor with high sensitivity and chemical specificity. Ethanol vapor is collected by passing ambient air into and through adsorber 114 (indicated as method step 310). The IR detector 126 provides an output voltage (designated $V_{off}$), with IR source 118 off (indicated as method step 312). The adsorber 114 is heated by heater 116 to release the captured ethanol vapor (indicated as method step 314). The IR source 118 is activated and an output voltage (designated $V_{on}$) of IR detector 126 is measured without having concentrated ethanol vapor in IR absorption cell 120 (indicated as method step 316). At a predetermined time, air flow is activated just long enough to transfer concentrated ethanol vapor from adsorber 114 into IR absorption cell 120 (indicated as method step 318). Next, the change in output voltage (designated $V_{sig}$) of IR detector 126 caused by the additional infrared adsorption, relative to $V_{on}$, is measured (indicated as method step 320). As the concentration of ethanol vapor in the tube increases, there is a decrease in the IR intensity that is detected. Microcontroller 140 calculates the ratio $V_{sig}/(V_{on}-V_{off})$ (indicated as method step 322). By activating the air flow just long enough to transfer concentrated ethanol vapor from adsorber 144 into IR absorption cell 120, the IR transmission can be measured for a predetermined or long period of time. This can increase detection sensitivity.

Air flow is activated again to purge adsorber 114 and IR absorption cell 120 of any concentrated ethanol vapor (indicated as method step 324).

Experiments

A further understanding of the above description can be obtained by reference to the following experimental result examples that are provided for illustrative purposes and are not intended to be limiting.

Figure 4:
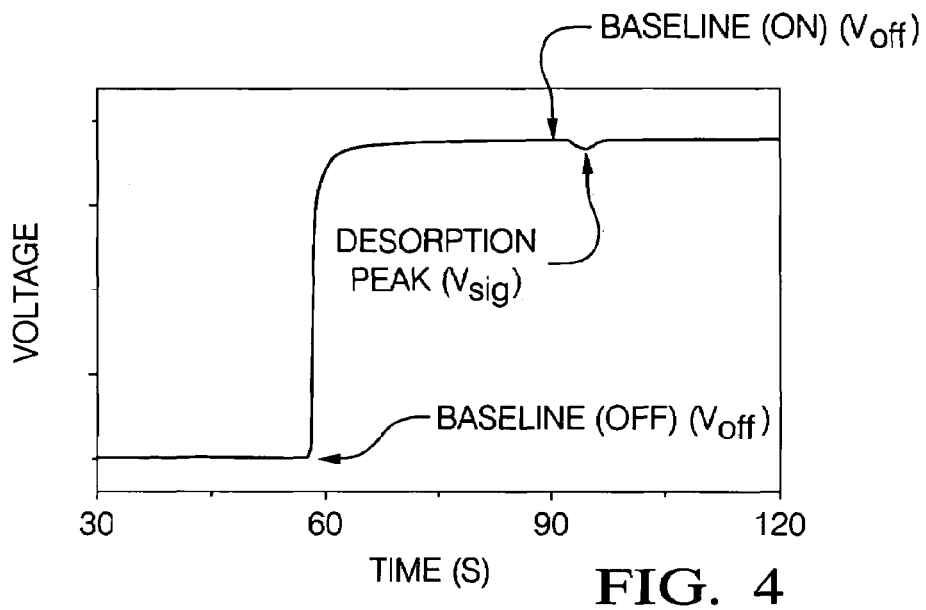
FIG. 4 is a graphical illustration of an example measured voltage as a function of time from the IR detector as in FIG. 1, the chemical sensor being sensitive to ethanol utilizing the method steps as in FIG. 2, in accordance with an embodiment of the present invention.

Referring to FIG. 4, a graphical illustration is presented of an example measured voltage as a function of time from IR detector 126 as in FIG. 1. In this example, chemical sensor 100 is sensitive to ethanol and utilizes the method steps as described in FIG. 2. As indicated in FIG. 4, "baseline off" extends to about 58 seconds, and then a rise in voltage is observed. "Baseline off" corresponds to the time that IR detector 126 provides a measured output (designated $V_{off}$), with IR source 118 off. At about 58 seconds, IR source 118 is activated. At about 90 seconds, the output of IR source 118 substantially levels off having air in the IR cell absorption cell 120, as indicated as "baseline on." The output from IR detector 126 at this time is designated $V_{on}$. With IR source 118 on, at a predetermined time, concentrated ethanol vapor is passed from adsorber 114 into and through IR absorption cell 120, and a dip in IR transmission is observed. The dip in output from IR detector 126 is indicated as "desorption peak." The change in IR detector 126 output (designated $V_{sig}$) is caused by the additional infrared adsorption that occurs, relative to $V_{on}$.

For a sensor that utilizes IR adsorption to determine ethanol concentration, it is desirable that the output be the ratio of two measured quantities. Such a ratio eliminates the gradual drift in calibration that can occur in response to changes such as aging of the light source or accumulation of material that adsorbs infrared on the optics. The chemical sensor 100 output provided by the present invention is a ratio. The numerator of the ratio is the integrated "desorption peak" versus time (relative to "baseline on"). The denominator is the difference between "baseline on" and "baseline off."

It is to be appreciated that a single channel of IR detection is employed by the present invention, and consequently the chemical sensor 100 is less costly to implement. Further, since a reference channel is made unnecessary, spurious infrared absorption at the IR wavelength of the reference channel is not a concern. Additionally, when measuring a chemical species, time resolution is not limited by the thermal time constant of IR source 118, resulting in a simplified system having improved performance.

Figure 5:
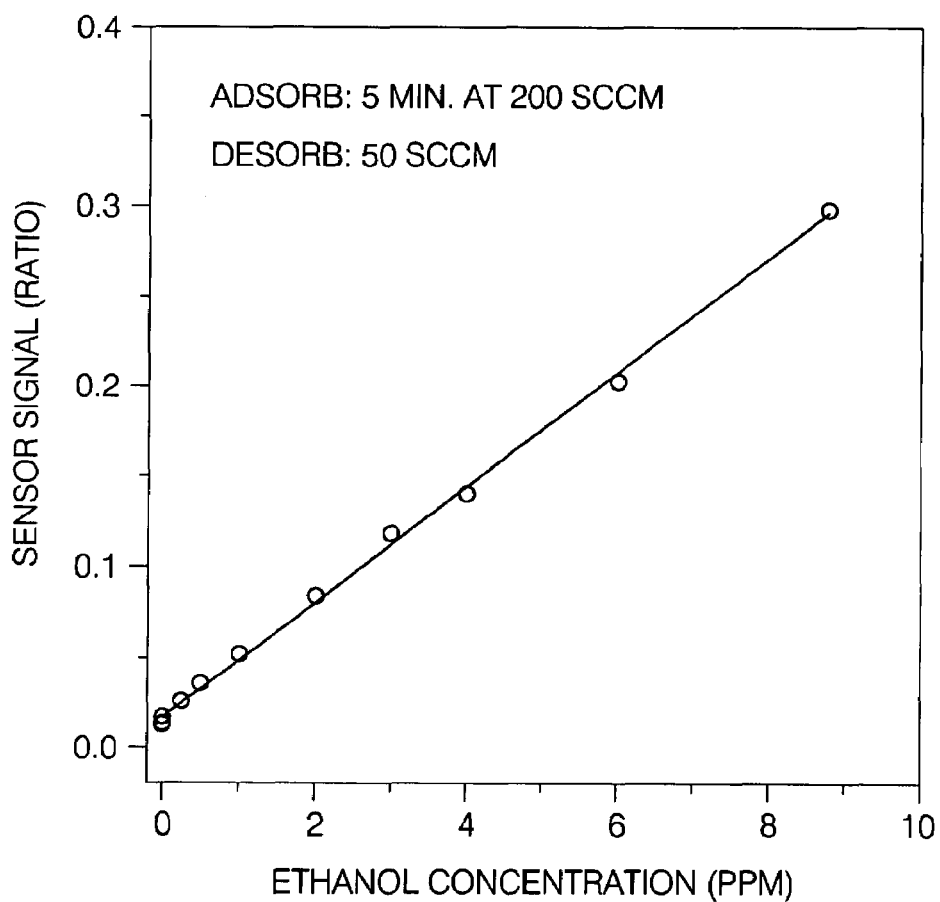
FIG. 5 is a graphical illustration of an example measured IR sensor signal ratio versus ethanol concentration obtained utilizing the method steps as in FIG. 2, in accordance with an embodiment of the present invention.

FIG. 5 is a graphical illustration of an example measured IR sensor signal ratio versus ethanol concentration obtained utilizing the method steps as in FIG. 2. As indicated on FIG. 5, ethanol vapor is collected by passing ambient air into and through adsorber 114 for 5 minutes at 200 sccm (standard cubic centimeter per minute). The flow is stopped while adsorber 114 is heated. Then, concentrated ethanol vapor is passed from adsorber 114 into and through IR absorption cell 120 at 50 sccm. This process is more fully described above with reference to FIG. 2.

Data was collected using known ethanol concentrations in the range of 0 to 9 ppm. This ethanol concentration range was selected for experiment since, as discussed above, for passive detection of ethanol, measurements of ethanol concentration in the range of 0.2 ppm to 10 ppm by volume is needed in the vehicle cabin. The data was used to obtain a best fit linear function of known ethanol concentration as a function of chemical sensor 100 output. In this example, the data showed that ethanol concentration was measured with a residual standard error of 0.13 ppm. The chemical sensor 100 (as in FIG. 1) satisfactorily measures ethanol concentration in the range of 0.1 ppm to 10 ppm, and therefore provides sufficient sensitivity for passive detection of an intoxicated motor vehicle driver. Additionally, since drivers can exhibit a BAC of much greater than 0.08, and the vehicle cabin air may be less diluted, the present invention further provides for measuring ethanol concentrations greater than 10 ppm.

Moreover, ethanol measurements can vary a small amount depending on measurement conditions. For example, the longer the interval between ethanol concentration measurements, the less standard deviation observed. In an experiment, when ethanol concentration measurements were performed at 62 seconds, the standard deviation of the ethanol measurements, after calibration, relative to a known concentration was 0.20 ppm. When ethanol concentration measurements were performed at 180 seconds, the standard deviation of the ethanol measurements, after calibration, relative to a known concentration was 0.16 ppm. Whereas, when ethanol concentration measurements were performed at 230 seconds, the standard deviation of the ethanol measurements, after calibration, relative to a known concentration was 0.08 ppm.

A person with ethanol in their blood tends to evaporate ethanol vapor from their skin into fresh air. Ethanol leaves the body through the skin in two ways. Ethanol in the blood can diffuse through the skin to directly enter the air as ethanol vapor. Additionally, under some circumstances, liquid sweat is formed. Liquid sweat contains ethanol at the same concentration as blood. Ethanol in sweat evaporates to form ethanol vapor in the air. However, the fraction of ingested alcohol that escapes through the skin is only about 1%, so it does not have a significant effect on the average concentration of ethanol vapor in a vehicle cabin. For these reasons, and more, the placement of the air intake 110 is important for more reliable ethanol concentration measurements.

Figure 6:
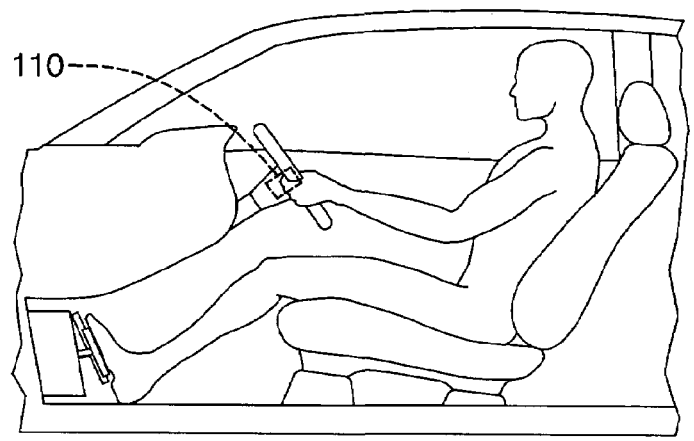
FIG. 6 is a diagrammatic view showing alternative placement options of the air intake for the vapor concentrator and the IR detector as in FIG. 1, in accordance with an embodiment of the present invention.
Figure 6:
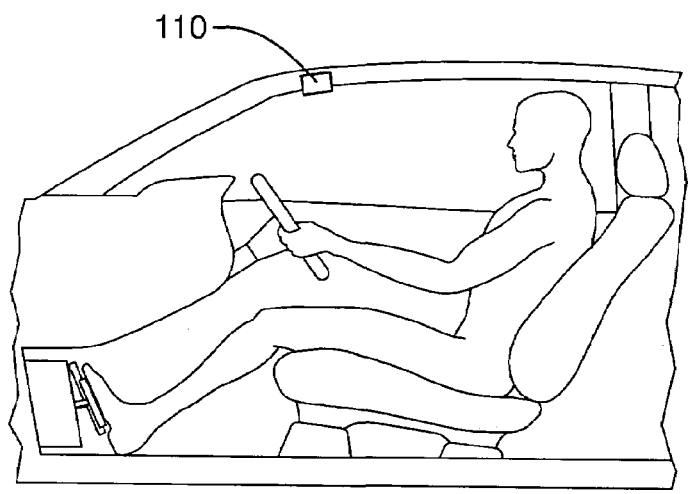
Figure 6:
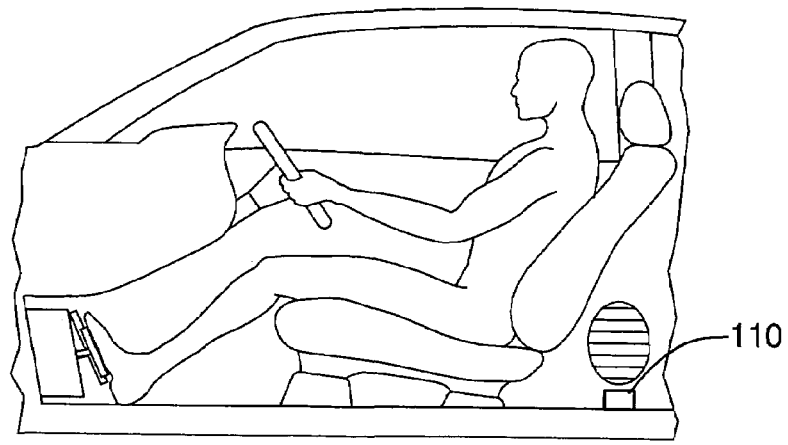

As illustrated in FIG. 6, the present invention provides alternative placement/mounting options of the air intake 110 in a vehicle cabin for the chemical sensor 100 as in FIG. 1.

It is important to note that exhaled breath from a vehicle driver is mixed with and diluted with air as it drifts to the ethanol sampling location (air intake 110). The dilution factor depends upon variables such as the speed of the fan blowing fresh air into the cabin, vehicle speed, the settings and directions of the air vents, and the location of the driver's mouth relative to the ethanol sensor. In a simple approximation, breath and air are fully mixed in the cabin before they arrive at the ethanol sensor. An adult male driver typically exhales 10.8 L/min; an adult female driver 9.0 L/min. The maximum air flow from the HVAC (heat-ventilation and air-conditioning) system into a vehicle is typically 250 to 300 cfm (7.08 to 8.50×103 L/min). This suggests that in steady state, the dilution factor could be as low as $1.3 \times 10^{-3}$, and that a passive ethanol sensor should be capable of measuring ethanol vapor concentrations as low as 0.3 ppm. Further, the volumetric breathing rate varies from person to person and is related to physical exertion. The volumetric breathing rate of a subject person must be accounted for to determine the minimum ethanol concentration that is needed for detection.

The vehicle driver's BAC is measured by sensing the concentrations of ethanol vapor in air sampled near the driver. The present invention can measure ethanol vapor concentration at one or more location in the vehicle cabin by placement of air intake 110 in one or more vehicle cabin locations. Further, the chemical sensor 100 can be situated in an inconspicuous location and operate independently without requiring active involvement by a driver.

For maximized ethanol sensitivity to the vehicle driver, it is preferable for the sensor to be exposed to the driver's breath before the driver's breath completely mixes with cabin air. Additionally, since a driver and a number of passengers may be present in the vehicle cabin, in an embodiment of the present invention, the air intake 110 is situated directly adjacent to a vehicle driver. For example, as shown in a), the air intake 110 is incorporated into the vehicle steering wheel or steering column. Additional air intake 110 placement locations are shown in FIG. 6, indicated as b) and c). Air intake 110 as shown in b) can be incorporated into the vehicle ceiling or dashboard (preferably distant to an air exhaust vent). Further, air intake 110 can be incorporated into the vehicle steering column, steering wheel, headrest, seat, A pillar or B pillar. Alternatively, air intake 110 can be incorporated into a vehicle body intake vent as shown in c).

Figure 7:
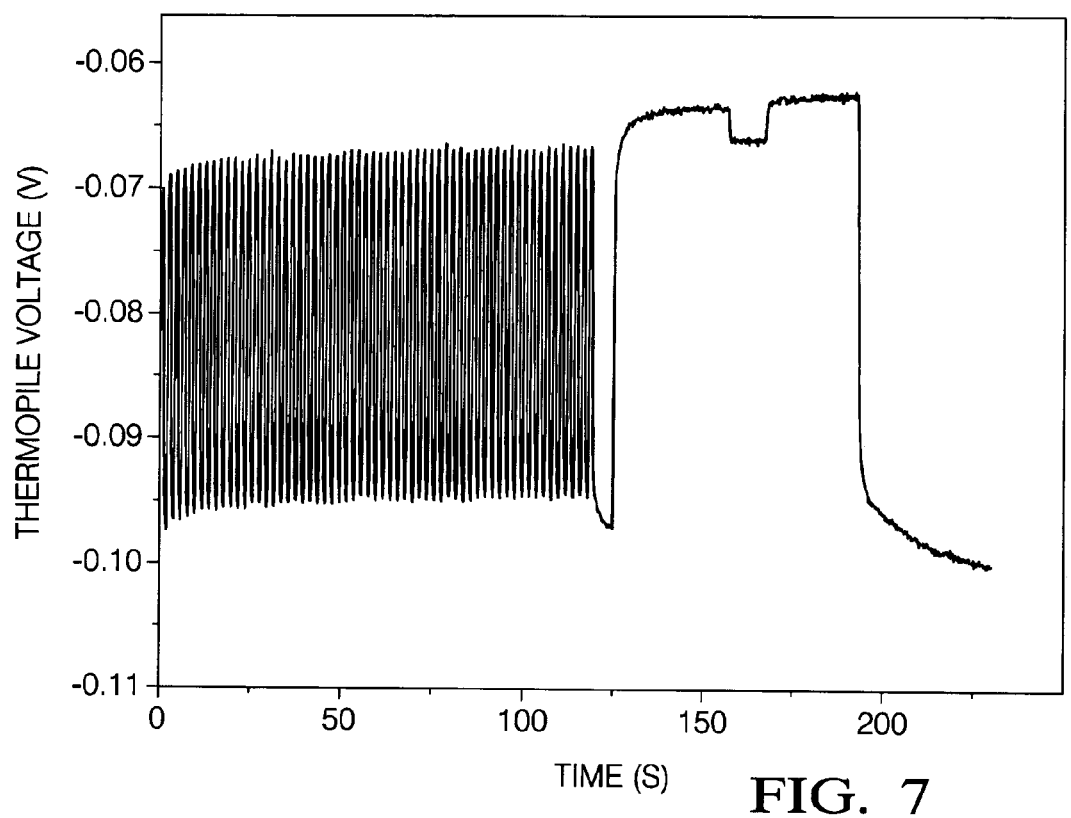
FIG. 7 is a graphical illustration of an example measured voltage as a function of time from the IR detector as in FIG. 1, the chemical sensor being sensitive to ethanol utilizing the method steps as in FIG. 3, in accordance with an embodiment of the present invention.

Referring to FIG. 7, a graphical illustration is presented of an example measured voltage as a function of time from the IR detector 126 as in FIG. 1. The chemical sensor 100 is sensitive to ethanol, utilizing the method steps as in FIG. 3. In this particular example, the ethanol concentration in the air is 4.3 ppm.

$CO_2$ is also measured by pulsing IR source 118 on and off as air is passed through adsorber 114 and IR absorption cell 120. $CO_2$ is not adsorbed by adsorber 114. The resulting effect of this pulsing can be observed from about time=0 to time=120, as the voltage jumps to about −0.068 V. Next (as more fully described in FIG. 3), IR source 118 is turned off for about 5 seconds to obtain a "baseline off" value. Subsequently, IR source 118 is activated and adsorber 114 is heated for a predetermined time. The IR detector 126 output voltage is elevated to the "baseline on" value. About 3 seconds later, air pump 130 is activated for 0.2 seconds, transferring concentrated ethanol vapor into IR absorption cell 120, causing the IR transmission to decrease to a constant value. This constant decreased IR detector 126 output voltage can be maintained as long as the concentrated ethanol vapor remains in IR absorption cell 120, as desired. Next, air pump 130 is activated purging adsorber 114 and IR absorption cell 120 of concentrated ethanol vapor. The IR detector 126 output voltage returns to its elevated "baseline on" value. Subsequently, at about 195 seconds, the IR source 118 is turned off and the IR detector 126 output voltage drops. Again, it is to be appreciated that the time periods described in FIG. 7, as well as other time periods described herein, are provided for illustrative purposes and are not intended to be limiting. Other time periods can be employed.

Figure 8:
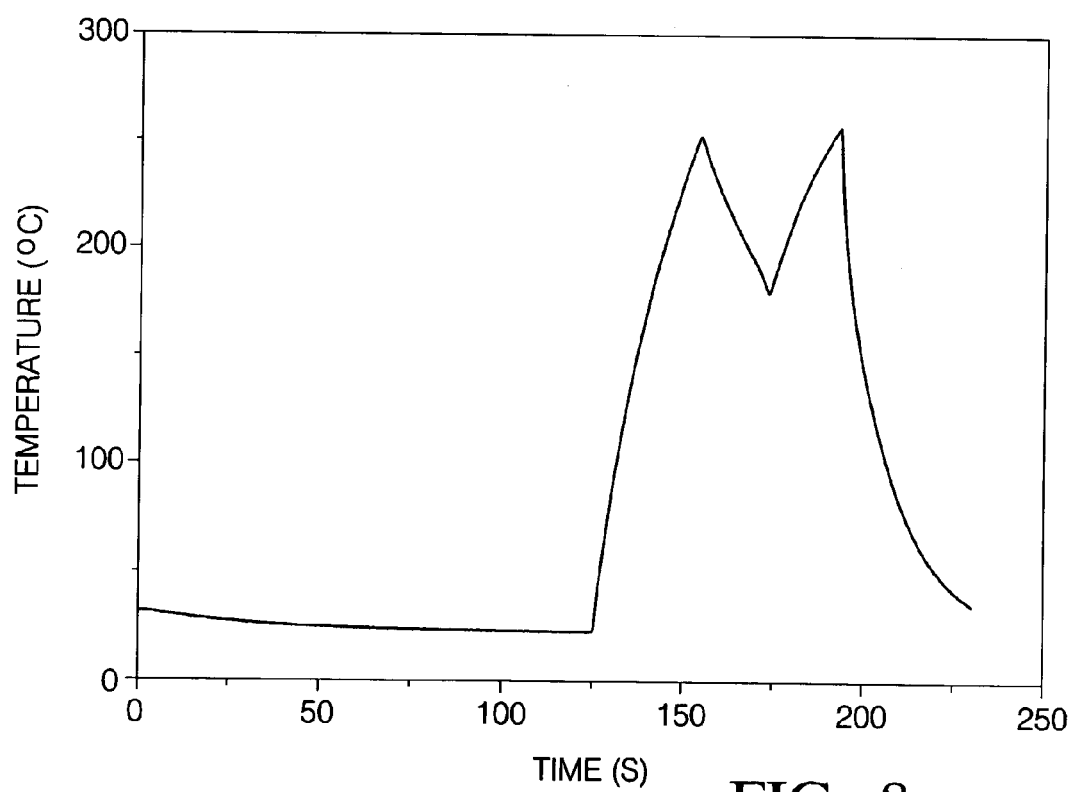
FIG. 8 is a graphical illustration of an example measured temperature as a function of time of the vapor concentrator adsorber of FIG. 1, in accordance with an embodiment of the present invention.

FIG. 8 is a graphical illustration of an example measured temperature as a function of time of the vapor concentrator adsorber 114 of FIG. 1. As described in FIG. 7, IR source 118 is activated and adsorber 114 is heated. Adsorber 114 is heated to about 250° C., although other heating temperatures may be useful. As may be observed in FIG. 8, a temperature increase occurs at about 125 seconds. This is consistent with the increase in voltage of FIG. 7 at the time when IR source 118 is activated. Heater 116 is subsequently turned off at 3 seconds prior to activating air pump 130 for 0.2 seconds to transfer the concentrated ethanol vapor into IR absorption cell 120. A drop in the temperature of adsorber 114 may be observed. Heater 116 is turned off in part to minimize any noise while IR detector 126 makes a measurement, although noise has not been observed. Next, when adsorber 114 is being purged of concentrated ethanol vapor, heater 116 is activated. A rise in the temperature of adsorber 114 may again be observed. Subsequently, at about 195 seconds, when IR source 118 is turned off, a fan (not shown) can be employed to help cool adsorber 114 to ambient temperature.

Other features and advantages of this invention will be apparent to a person of skill in the art who studies this disclosure. For example, it is to be appreciated that on-board ethanol vapor sensors could use a vapor concentrator in conjunction with alternative detection devices including a floating-gate field effect transistor, a gas chromatograph, a heated metal-oxide film sensor, a sensor that measures oxidation luminescence, a CMOS capacitive sensor that uses a polymer film, and a photoacoustic sensor. Further, higher sensitivity is also possible with more elaborate spectroscopic techniques. If a narrow-line laser source is used, its optical frequency can be tuned to one side of a narrow feature in the spectrum, and the laser frequency can be swept back and forth to modulate the transmitted intensity. Sensitivity improves by orders of magnitude if the gas to be analyzed is at a pressure on the order of 1 Pa. Thus, exemplary embodiments, modifications and variations may be made to the disclosed embodiments while remaining within the spirit and scope of the invention as defined by the appended claims.

We claim:

1. A chemical vapor sensor comprising:
   an infrared source for generating infrared waves;
   an infrared detector in optical communication with the infrared source, and configured to measure the intensity of the infrared waves generated from the infrared source;
   a vapor concentrator comprising:
     a vapor adsorber;
     a heating source to heat the vapor adsorber;
   an infrared absorption cell in optical communication between the infrared source and infrared detector, and defining an inlet for taking in air from the vapor concentrator, and an outlet for expelling air, wherein the infrared waves pass through the infrared absorption cell;
   an air flow source configured to control air flow through the vapor adsorber and through the infrared absorption cell; and
   a microcontroller configured to control the air flow source, such that the air flow source is activated to flow air into the vapor concentrator, deactivated when the heating source is heating the vapor adsorber, which releases a concentrated vapor from the air, activated to flow the concentrated vapor into the path of the infrared waves in the absorption cell, deactivated when the infrared detector measures the intensity of the infrared waves that pass through the infrared absorption cell and the concentrated vapor, and activated to purge the infrared absorption cell.

2. The chemical vapor sensor as in claim 1, further comprising:
   an infrared filter for selecting a range of infrared frequency or wavelength that is adsorbed by a predetermined chemical species of interest.

3. The chemical vapor sensor as in claim 1, wherein the vapor concentrator, infrared source, and infrared detector measure ethanol vapor.

4. The chemical vapor sensor as in claim 3, wherein the ethanol vapor is sampled from the cabin of a vehicle without requiring active involvement of a vehicle driver.

5. The chemical vapor sensor as in claim 3, wherein the infrared detector measures ethanol concentration in air of at least 0.1 parts per million (ppm).

6. The chemical vapor sensor as in claim 5, wherein the infrared detector measures ethanol concentration in air of 0.1 ppm to 10 ppm, including a standard deviation.

7. The chemical vapor sensor as in claim 1, wherein the vapor adsorber material is one of carbon, carbon molecular sieves, activated carbon, carbon nanotubes, porous organic polymer, inorganic materials having a high surface area and zeolite.

8. The chemical vapor sensor as in claim 3, further comprising a microcontroller for instructing and carrying out a safety system response if a predetermined ethanol concentration is exceeded in the vehicle cabin, wherein the safety response includes increasing a minimum headway distance behind a preceding vehicle, constraining vehicle performance, transmitting vehicle cabin ethanol measurements to police and to a vehicle recorder.

9. A passive chemical vapor sensor for sampling ethanol vapor from a vehicle cabin comprising:
   an infrared source for generating infrared waves;
   an infrared detector in optical communication with the infrared source and configured to measure the intensity of the infrared waves generated from the infrared source;
   an infrared filter for selecting a range of infrared frequency or wavelength that is adsorbed by a predetermined chemical species of interest;
   an infrared absorption cell in optical communication between the infrared source and the infrared detector, and defining an inlet for taking in air, and an outlet for expelling air, wherein the infrared waves pass through the infrared absorption cell;
   a vapor concentrator in communication with the infrared absorption cell, comprising:
     a vapor adsorber; and
     a heating source to heat the vapor adsorber;
   an air flow source for controlling air flow through the vapor adsorber and through the infrared absorption cell; and
   a microcontroller configured to control the air flow source, such that the air flow source is activated to flow air into the vapor concentrator, deactivated when the heating source is heating the vapor adsorber, which releases a concentrated vapor, activated to flow the concentrated vapor into the path of the infrared waves in the absorption cell, wherein the infrared detector measures the intensity of the infrared waves that pass through the infrared absorption cell and the concentrated vapor, and activated to purge the infrared absorption cell.

10. The passive chemical vapor sensor as in claim 9, wherein the infrared detector measures ethanol concentration in air of at least 0.1 parts per million (ppm).

11. The passive chemical vapor sensor as in claim 10, wherein the infrared detector measures ethanol concentration in air of 0.1 ppm to 10 ppm, including a standard deviation.

12. The passive chemical vapor sensor as in claim 9, wherein the vapor adsorber material is one of carbon, carbon molecular sieves, activated carbon, carbon nanotubes, porous organic polymer, inorganic materials having a high surface area, and zeolite.

13. The passive chemical vapor sensor as in claim 9, further comprising a microcontroller for instructing and carrying out a safety system response if a predetermined ethanol concentration is exceeded in the vehicle cabin, wherein the safety response includes increasing a minimum headway distance behind a preceding vehicle, constraining vehicle performance, transmitting vehicle cabin ethanol measurements to police and to a vehicle recorder.

14. The passive chemical vapor sensor as in claim 9, wherein the infrared detector utilizes a single absorption channel for infrared detection.

15. The passive chemical vapor sensor as in claim 9, wherein the inlet is situated in one of the vehicle cabin ceiling, dashboard, steering column, steering wheel, headrest, seat, A pillar, B pillar, and air intake vent.

16. A method of measuring a chemical vapor concentration comprising:

passing air, including sample vapor, by an air flow source through an adsorber;

measuring an output (designated $V_{off}$) of an infrared detector, with an infrared source deactivated;

heating the adsorber, wherein the air flow source is deactivated while the adsorber is heated;

measuring an output (designated $V_{on}$) of the infrared detector, with the infrared source activated;

passing concentrated sample vapor from the adsorber into and through the infrared absorption cell at a predetermined time, which comprises the steps of:

activating the air flow source long enough to transfer concentrated sample vapor from the adsorber into the infrared absorption cell;

holding the concentrated sample vapor in the infrared absorption cell for a predetermined time by deactivating the air flow source; and activating the air flow source again to purge the adsorber and the infrared absorption cell of the concentrated sample vapor;

measuring a change in an output (designated $V_{sig}$) of the infrared detector; and calculating the ratio $V_{sig}/(V_{on}-V_{off})$.

17. The method of measuring a chemical vapor concentration as in claim 16, wherein passing air, including sample vapor, through an adsorber comprises passing vehicle cabin air through an adsorber, and wherein the sample vapor is ethanol vapor.

18. The method of measuring a chemical vapor concentration as in claim 16, wherein calculating the ratio $V_{sig}/(V_{on}-V_{off})$ comprises utilizing a microcontroller.

19. The method of measuring a chemical vapor concentration as in claim 16, further comprising at least one of:

heating the infrared absorption cell to a temperature above the dew point of the sample vapor;

heating the adsorber on the order of 10 degrees Celsius above ambient temperature while the sample vapor is being adsorbed;

coating the inside of the infrared absorption cell with a material that prevents water droplets from nucleating;

altering the air flow through the infrared absorption cell wherein exhaust from the adsorber flows down the center of the infrared absorption cell and avoids contacting cool infrared absorption cell walls; and forming the adsorber from a material that is more hydrophobic than carbon.

20. The method of measuring a chemical vapor concentration as in claim 16, further comprising amplifying the partial pressure of the sample vapor by at least one of isolating the adsorber as it is heated, and rapidly heating the adsorber while maintaining a constant flow of air through the adsorber.

21. The method of measuring a chemical vapor concentration as in claim 17, further comprising repetitively performing ethanol vapor detection during vehicle operation.

22. The chemical vapor sensor as in claim 1, wherein the air flow source is activated just long enough to flow the concentrated vapor from the vapor concentrator to the infrared absorption cell.

23. The passive chemical vapor sensor as in claim 9, wherein the air flow source is activated just long enough to flow the concentrated vapor from the vapor concentrator to the infrared absorption cell.

* * * * *